United States Patent [19]

Aiba

[11] Patent Number: 5,551,873
[45] Date of Patent: Sep. 3, 1996

[54] DETECTOR OF THE CLASP REGION OF A DENTURE

[75] Inventor: Tatsuya Aiba, Shizuoka, Japan

[73] Assignee: Ltd. Aibagiken, Shizuoka, Japan

[21] Appl. No.: 329,469

[22] Filed: Oct. 26, 1994

[51] Int. Cl.⁶ ................................................. A61C 19/04
[52] U.S. Cl. ................................................. 433/72; 33/514
[58] Field of Search ........................ 433/72, 75; 33/513, 33/514, 783, 784, 810, 811

[56] References Cited

U.S. PATENT DOCUMENTS

| | | | |
|---|---|---|---|
| 1,901,724 | 3/1933 | Bennett | 33/513 |
| 2,528,053 | 10/1950 | Harris | 433/75 |
| 3,330,038 | 7/1967 | Berman | 433/72 |
| 3,417,471 | 12/1968 | Mitchell | 433/72 |
| 4,277,237 | 7/1981 | Dermer | 433/72 |

FOREIGN PATENT DOCUMENTS

| | | | |
|---|---|---|---|
| 1412770 | 7/1988 | U.S.S.R. | 433/75 |
| 2188426 | 9/1987 | United Kingdom | 33/784 |

OTHER PUBLICATIONS

"Clasp Denture Providing a Rotational Path for the Mounting/Demounting of a Denture", Quintessence of Dental Technology, Dec. 1989, p. 1523.

*Primary Examiner*—Ren Yan
*Attorney, Agent, or Firm*—Jacobson, Price, Holman & Stern, PLLC

[57] ABSTRACT

A detector for detecting the optimum region for hooking a clasp of a removable partial denture to a tooth model has first and second pointed sensing elements adjustably mounted on a horizontal beam structure. The beam structure may have a single beam or multiple beams linked in parallel and the beam structure is suspended from a holder above the model by an installation member which includes a swivel joint for rotating the beam structure about a horizontal axis.

5 Claims, 5 Drawing Sheets

FIG. 7
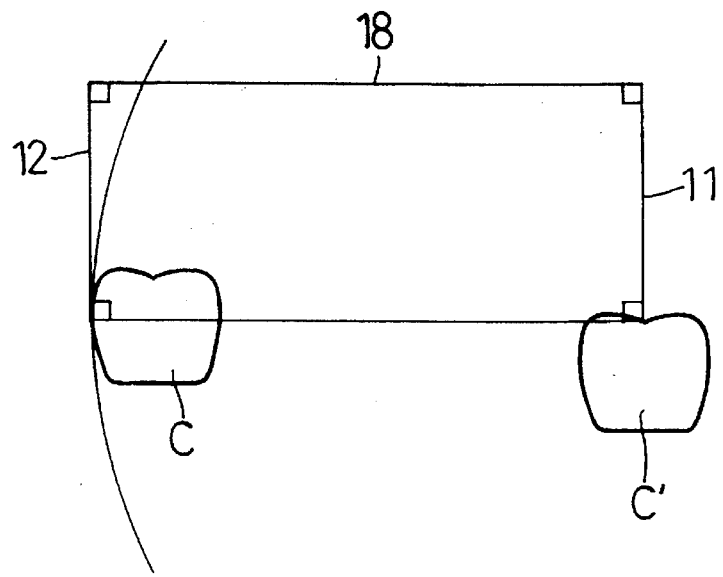
FIG. 8(a)     FIG. 8(b)     FIG. 8(c)
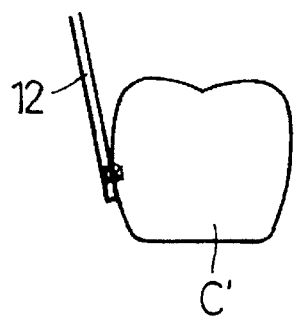 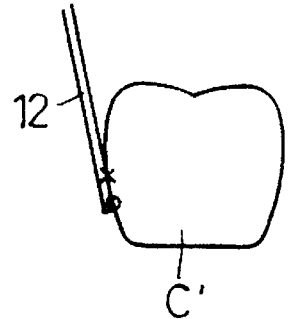 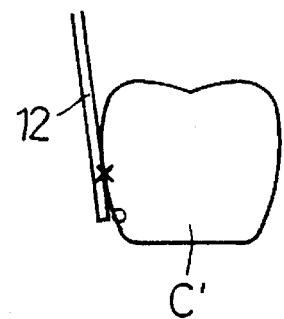

5,551,873

DETECTOR OF THE CLASP REGION OF A DENTURE

BACKGROUND OF THE INVENTION

1. Field of the Invention

The present invention relates to an instrument for molding a model by patterning a dentition of a patient with missing teeth and detecting a region for hooking a clasp that is a fixing means onto a tooth corresponding to an abutment tooth of the model for fixing a removable partial denture for filling up the missing teeth.

2. Description of Prior Art

In terms of dental technology, it is important to determine the mounting/demounting direction of a denture when constructing a removable partial denture, and a method of investigating the set state of an abutment tooth through the use of a model surveyor 1 shown in FIG. 1 has been heretofore adopted. In this method, a detecting needle referred to as an analyzing rod is applied to the side of an abutment tooth, the point of a clasp is hooked onto an undercut located under a contact point, and the denture is held in place by the elasticity of the clasp. Although it is conceivable that a denture thus designed is mounted/demounted in a direction parallel to the analyzing rod, the denture is moved out of place by the application of alternate side-to-side rotational motion. The conventional denture design, however, rotational motion is not analyzed thoroughly. In addition, as described in "Clasp Denture Providing a Rotational Path for the Mounting/Demounting of a Denture" (Quintessence of Dental Technology, December 1989, page 1523), among others, an interest has arisen in a mounting/demounting method for denture utilizing a rotational path, but instruments and apparatuses for executing such a method have not yet been proposed.

SUMMARY OF THE INVENTION

The present invention has been developed in view of the above points, and its object is to make it possible to accurately determine optimum region for hooking a clasp that is a means for fixing a removable partial denture onto a abutment tooth.

Further, it is another object of the present invention to make it possible to confirm the proper operation of a removable partial denture with a clasp prearranged for mounting/demounting through rotational movement by installing it on a model, and to realize necessary and sufficient maintaining strength when it is installed on an actual tooth in the oral cavity.

Above and other objects have been attained by such means that a detector of the clasp region of a denture composed of a first sensing element 11 for abutting a point against the top surface of another tooth C' that becomes the center of rotational movement for mounting/demounting the clasp onto and from a tooth C corresponding to the abutment tooth through an installation method utilizing the rotational path, a second sensing element 12 capable contacting the side of the tooth C where the clasp is hooked in parallel with the first sensing element 11, a supporting body 13 for making either the first or second sensing elements 11 and 12 fixable and mounting the other so that it is accessible and separable while maintaining a parallel state between both sensing elements, and an installation member 14 fitted so that it may rotate on the supporting body 13 for arranging the first and second sensing elements 11 and 12 above a model B that is positioned with its face upward.

BRIEF DESCRIPTION OF THE DRAWINGS

FIG. 7 is an explanatory view showing a use state of the above; and

FIG. 8 is (a) an explanatory view showing an example requiring no retaining, (b) is an explanatory view showing an example requiring no retaining, and (c) is an explanatory view showing an example requiring retaining.

DETAILED DESCRIPTION OF THE PREFERRED EMBODIMENTS

Figure 1:
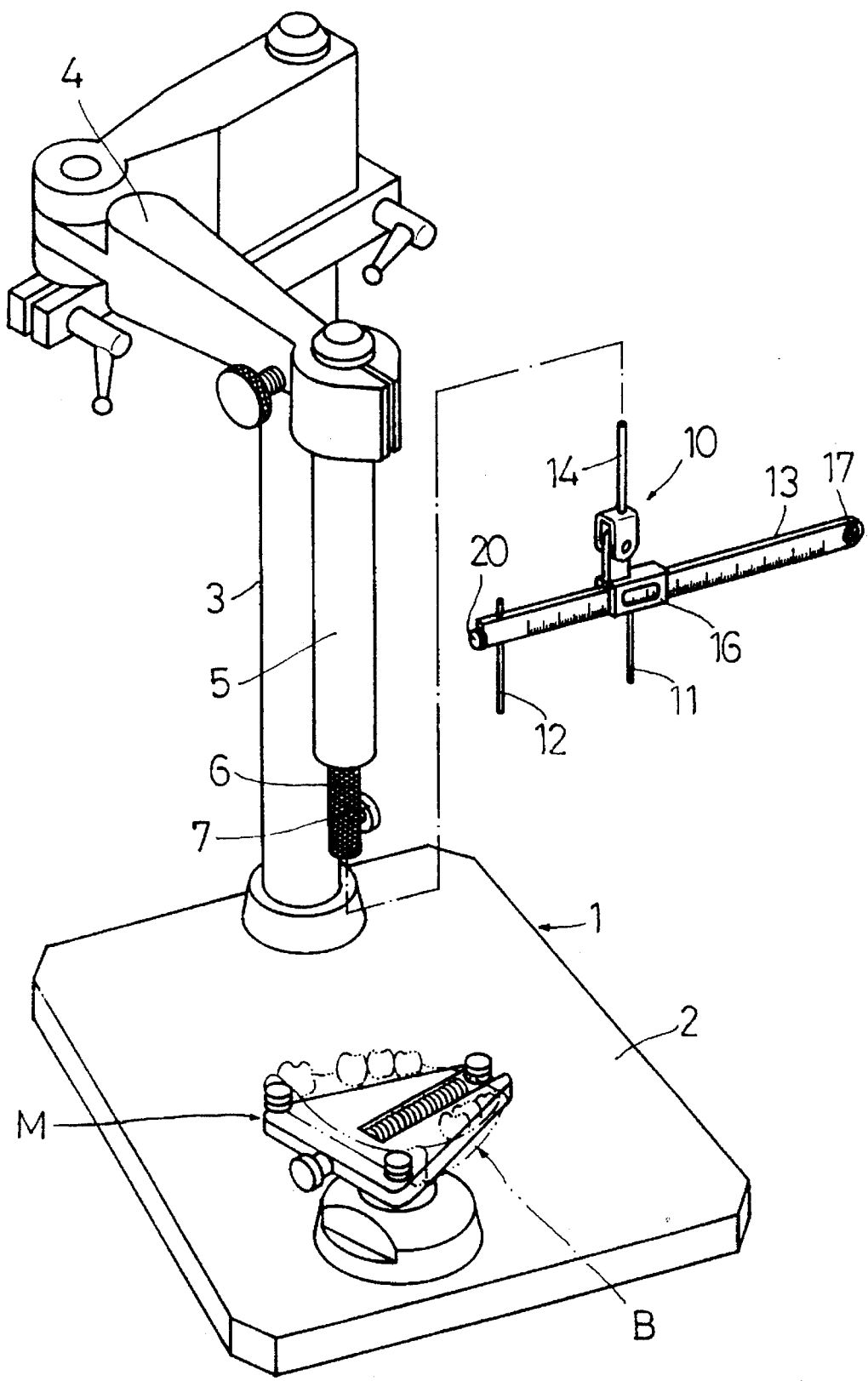
FIG. 1 is a perspective view showing a detector and surveyor according to a first embodiment of the present invention.

A surveyor i used as a model surveyor and a model table M for setting a plaster model B in an oral cavity to construct a denture are shown in FIG. 1, and they are used together with a detector 10 of a denture clasp region according to the present invention. The surveyor 1 features a base 2 and a columnar body 3 positioned at the rear section thereof, and a supporting rod 5 is attached to the columar body 3 perpendicularly so that it is movable upward and downward through a bending arm 4. Reference numeral 6 represents a shaft holder, which features an insertion port for the shaft at its lower end thereof, and fixes an inserted shaft like installation member with a set screw 7, as described later. In addition, the respective parts of the above-described structure can be fixed as required.

Figure 2:
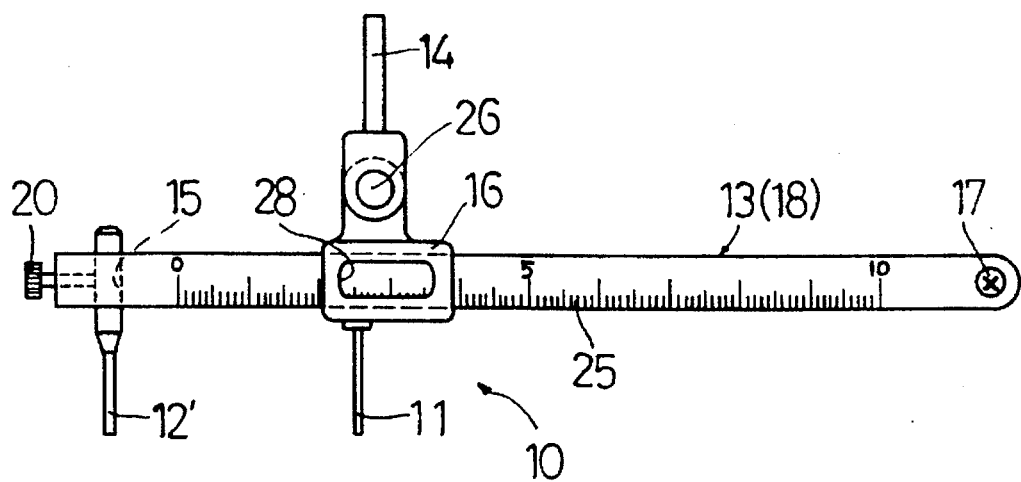
FIG. 2 is a front view of a detector of a first embodiment.

The detector 10 shown in FIGS. 1 and 2 relates to a first embodiment of the present invention, and features a supporting body 13 composed of just one thin rectilinear member extending from side to side. This supporting body 13 is made of a rigid material, is of a sufficient length to cover the teeth in the oral cavity, and features a scale 25 provided along the length direction.

The first sensing element 11 is provided movably on the supporting body 13. Specifically, a slidable slider 16 is inserted along the length direction of the supporting body 13, and the first sensing element 11 projecting in a sliding direction, i.e., so that it meets at right angles with the length direction of the supporting body 13, is attached at the lower section of the slider to form one side of what is referred to as an analyzing rod. The first sensing element 11 is composed of a rigid needle-shaped member for abutting the point thereof against the top surface of the tooth C'. An installation member 14 for attaching the detector 10 to the surveyor 1 is supported so that it may rotate by means of a support shaft 26 at the upper part of the slider 16.

A second sensing element 12 arranged in parallel with the first sensing element 11 is attached at one end of the supporting body 13. A through port 15 into which the second sensing element 12 is inserted is formed upward and downward at the said end section, where the second sensing element 12 is inserted and the sensing element 12 is attached by a screw 20. In addition, the second sensing element 12 shown FIG. 1 in is made of a rigid needle-shaped member similar to the first sensing element 11 described above, but the second sensing element in FIG. 2 features a color-sensing element 12' marked with chalk at the point, and both sensing elements 12 and 12' are interchangeable with each other in the present invention.

In addition, a slip-out preventer 17 for the slider 16 attached to the first sensing element 11 is provided at the other end of the supporting body 13. Further, a window 28 is located on the slider 16 so as to be convenient for determining the position of the first sensing element 11 on the scale 25.

It is possible to sufficiently achieve the object of the present invention by means of the detector 10 according to the first embodiment described above. In such a case, however, the premise is that the surveyor 1 shown in FIG. 1 must be used together with the detector 10. Because the illustrated surveyor 1 features an expansion arm 4 and a vertically movable supporting rod 5, a high degree of freedom is provided. On the other hand, it is possible to construct a detector according to a second embodiment shown in FIG. 3 when a surveyor is used that does not feature as high a degree of freedom of movement as the surveyor shown in FIG. 1.

A detector according to the second embodiment also features a structure in which slidable a first sensing element 11 is provided through the use of a slider 16 on a thin, straight beam 18, a vertical through hole 27 is formed at one end of the straight beam 18, and a second sensing element 12 is provided in parallel to the first sensing element 11 at that through hole 27, and is similar to the first embodiment in this respect. In the case of the second embodiment, however, a thin, straight beam 19 of the same shape as the straight beam 18 is located above the beam 18, they are connected by a short connecting beam 21 supported at another end portion, and a movable beam 23 is supported upward at one end of the lower straight beam 18 so as to create an overall parallel link shape. Thus, this detector features a supporting body 13 structured so as to allow a great degree of freedom.

Figure 3:
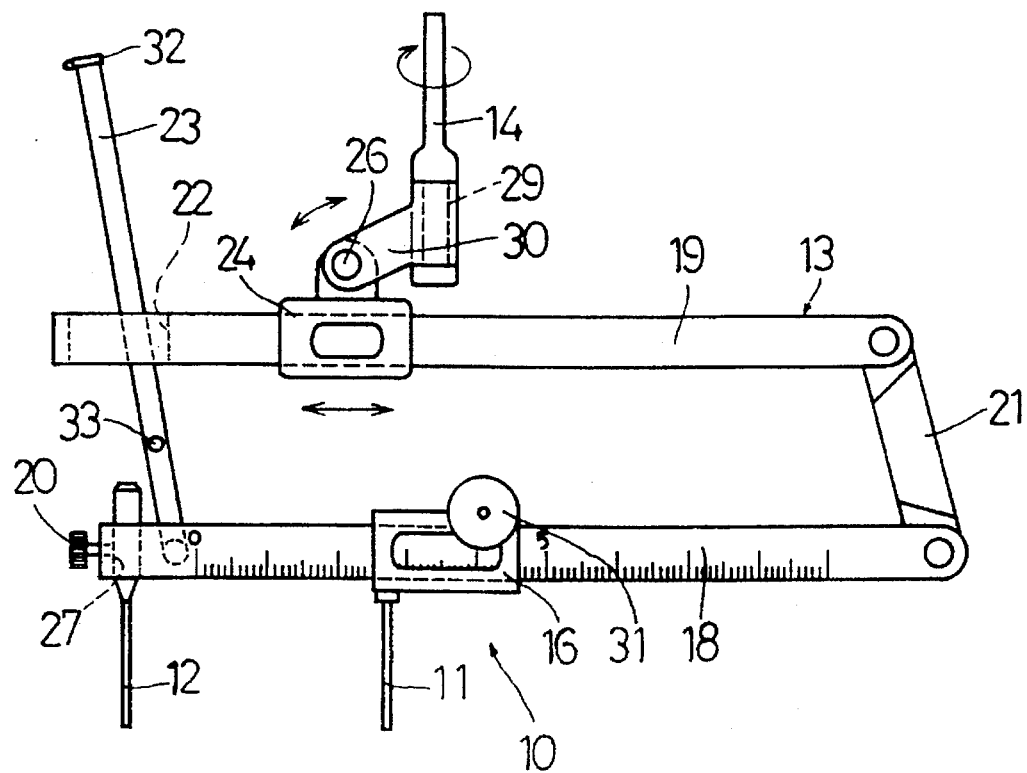
FIG. 3 is a front view of a detector of a second embodiment.

An installation member 14 is attached to the upper straight beam 19 of the supporting body through a slider 24 and a bearing arm 30. Thus, the member 14 is relatively movable along the length direction of the straight beam 19 similarly to the first sensing element 11, and is rotatable around two orthogonal axes 26, 29 that may meet with the straight beam 19 at right angles. In FIG. 3, the same reference numerals as for the first embodiment are adopted, and a detailed description thereof is omitted. In addition, 31 represents an operational knob provided on the slider 16 that includes the first sensing element 11. Numerals 32 and 33 represent stoppers, which prevent the movable beam 23 from slipping out upward or downward from the vertical longitudinal hole 22 formed at one end of the upper straight beam 19.

Figure 4:
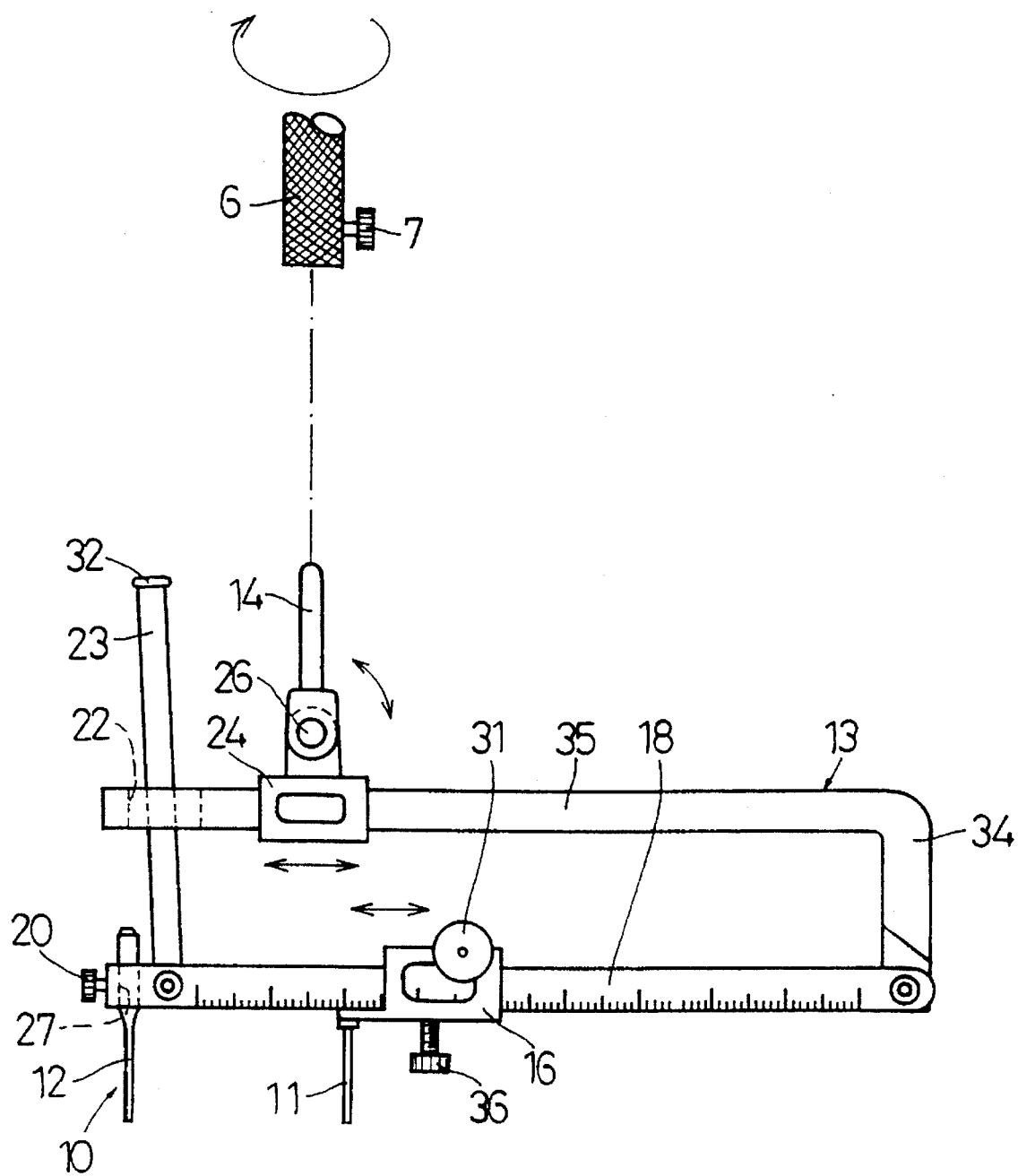
FIG. 4 is a front view of a detector of a third embodiment.

Further, a third embodiment of a detector according to the present invention will be described with reference to FIG. 4. The detector 10 according to a third embodiment features a structure in which a pin connection between the straight beam 19 and the short connecting beam 21 in the second embodiment is disused, an L-shaped bent tail 34 is provided at the end of a straight beam 35, and a set screw 36 is provided on the slider 16.

The detector 10 of the third embodiment is for a movable arm surveyor, and a shaft holder 6 attached after the installation member 14 has been inserted features a structure in which it is rotatable around the vertical axis. Since the structure other than shaft holder may be the same as the detector 10 of the first and second embodiments, a detailed description thereof is omitted and reference numerals are adopted.

The detector 10 according to the present invention thus structured is used for identifying the optimum clasp region that is a means for attaching a removable partial denture D for filling up a defective area of a dentition (missing teeth) with respect to a model B patterned from the inside of the oral cavity of a patient of denture construction. In the detector 10, the installation member 14 thereof is inserted into the shaft holder 6 of the surveyor 1 and is fastened with a screw 7. Any instrument may be used in the first, second, and third embodiments, but the description given here is for that of the second embodiment (FIG. 6).

Figure 5A:
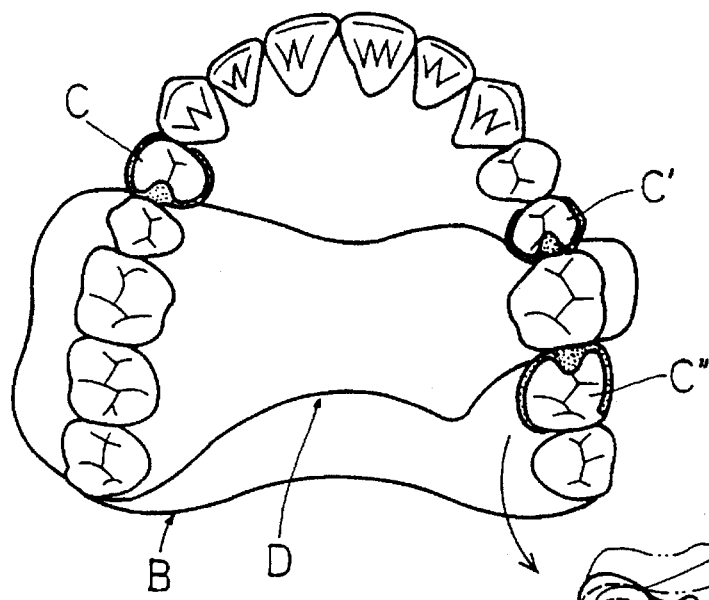
FIG. 5 is a plan view of a model and a removable partial denture in an oral cavity.
Figure 5B:
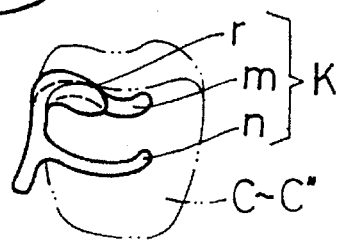
Figure 6:
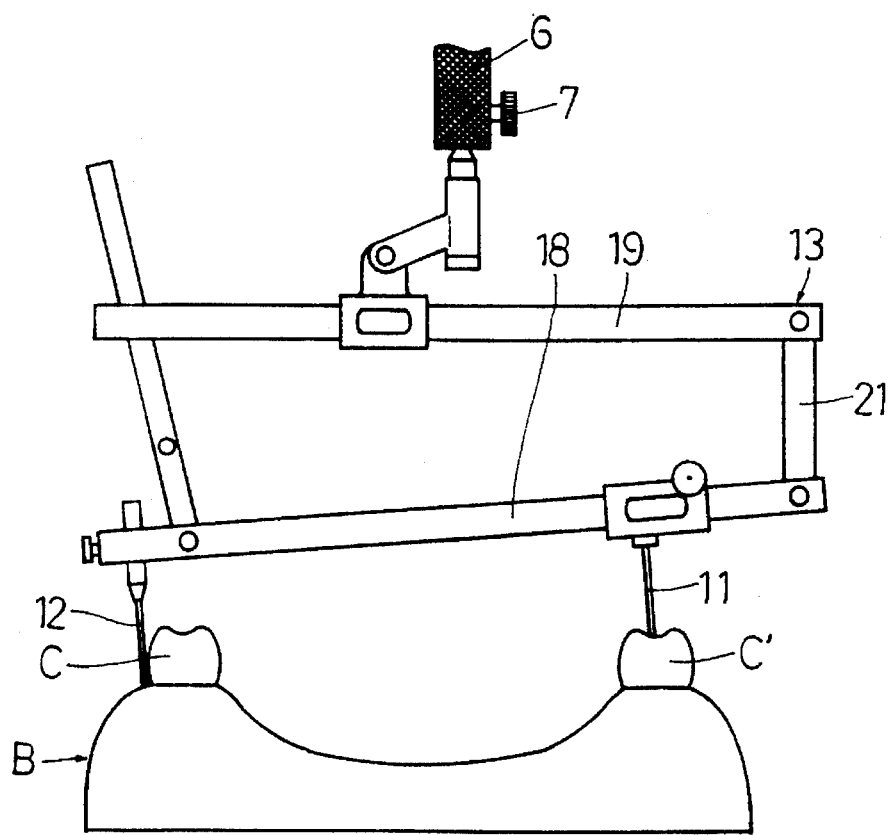
FIG. 6 is a front view showing a use state of the above.

When the model B is assumed to be an upper jaw model, as shown in FIGS. 5 and 6, the right first to fourth teeth, the left first to fifth teeth, and the left seventh and eighth teeth of the dentition are healthy teeth, and the right fifth to eighth teeth and the left sixth tooth are missing teeth. Therefore, it is an object of the detector 10 of the present invention to identify a clasp region for fixing the removable partial denture D composed of the right fifth to eighth teeth and the left sixth tooth in the oral cavity, the abutment teeth for obtaining retaining of the denture D are the right fourth tooth C, the left fifth tooth C', and the left seventh tooth C'' (see FIG. 5). The clasp K is fitted to the abutment tooth so as to surround it, and fixes the denture D so that it does not detach. The illustrated clasp K features left and right arm portions m and n hooked around the abutment tooth and a rest r for preventing the denture D from sinking by hooking it to the upper end of the abutment tooth.

In order to determine the optimum region in which to attach the clasp K to the abutment tooth, design is made first as usual manner, then the point of the first sensing element 11 is applied to the upper end of the abutment tooth C', which will become the center of rotation when the denture D is removed, where the rest r is attached (FIG. 5), and the second sensing element 12 is contacted with the is outer surface of the abutment tooth where the clasp K attached. At this time, a contact point between the second sensing element 12 and the abutment tooth C is marked on the side surface of a tooth (mark x in FIG. 8). It is possible to use the above-mentioned color-sensing element 12' for such marking. FIG. 8(a) shows a state in which a mark o in the clasp region determined through the use of the design as usual manner and the mark x on the contact point coincide with each other. Thus, retaining is impossible with this clasp. In FIG. 8(b), the second sensing element 12 is in contact with the mark o and the mark x, and it is clear that retaining is also not possible with this clasp. In FIG. 8(c), the contact point at the mark x of the second sensing element is apart outward of the clasp point at the mark o. Therefore, the clasp K comes under the undercut portion and is attached inside the rotational path. Thus, it is believed that anticipated retaining can be expected. Regarding the other abutment teeth C' and C'', the optimum clasp region also determined by is repeating operations similar to those described above.

Since the present invention is structured and acted as described above, it is possible to accurately determine in advance the optimum region in which the clasp that is a means for fixing the removable partial denture is hooked onto the abutment tooth. Accordingly, an effect is produced in which it is possible to fix the removable partial denture with a clasp that is prearranged so as to be mounted/demounted through rotational movement to the actual abutment tooth in the oral cavity with necessary and sufficient retaining strength.

What is claimed is:

1. A detector of the clasp region of a denture, for use with a model of an oral cavity for denture construction to identify a region to which a clasp can be hooked onto a first tooth corresponding to a abutment tooth for fixing a removable partial denture for a defective portion of a dentition, the detector comprising:

- a first sensing element having a pointed end for abutting against a top surface of another tooth that becomes a center of rotational motion for mounting/demounting the clasp onto and from said first tooth through a mounting/demounting method utilizing a rotational path;
- a second sensing element capable of contacting a side surface of said first tooth where the clasp is hooked in parallel with the first sensing element;
- a supporting body for the sensing elements for making one of the sensing elements fixable and fitting the other of the sensing elements in an accessible and separable manner while keeping both sensing elements in parallel; and
- an installation member attached to the supporting body for securing the supporting body in a holder with the first and second sensing elements above a model that is positioned facing upward on a model table, the supporting body being attached to the installation member by means of a swivel connection including a support shaft allowing rotational movement of the supporting body relative to the installation member about a substantially horizontal axis.

2. A detector according to claim 1, wherein the supporting body is composed of a thin, straight beam, the second sensing element is attached to the beam so that it may be mounted/demounted onto and from a small hole provided at right angles through the beam at one end section thereof, the first sensing element is attached to a slider mounted slidably along the beam and a stop for the slider is provided at an opposite end section of the beam.

3. A detector according to claim 1, wherein the supporting body is composed of upper and lower straight beams arranged in parallel, a short connecting beam pivotally connected to adjacent ends of the straight beams, and a movable beam having one end section rotatably connected to an opposite end of the lower straight beam and an upper part which projects upward through a longitudinal hole provided in the upper straight beam, the first and second sensing elements being on the lower straight beam, and the installation member being attached to the upper straight beam through a slider.

4. A detector according to claim 1, wherein the supporting body is composed of a first straight beam the first sensing element being attached to a slider mounted slidably along the first straight beam, the second sensing element being attached to one end of the first straight beam, a further straight beam with an L-shaped end section supported rotatably at an opposite end of the first straight beam, and a movable beam having one end supported rotatably at said one end of the first straight beam and an upper part of which projects upward through a longitudinal hole provided in the further straight beam.

5. A detector according to claim 1, wherein the second sensing element is attached by means of a screw at one end section of the supporting body so that it may be mounted/demounted and is replaceable by a color-sensing element.

* * * * *